(12) United States Patent
Guillot et al.

(10) Patent No.: US 9,476,817 B2
(45) Date of Patent: Oct. 25, 2016

(54) DETERMINATION OF INTERFACIAL TENSIONS IN SUPERCRITICAL CONDITIONS

(71) Applicants: RHODIA OPERATIONS, Aubervilliers (FR); CENTRE NATIONAL DE LA RECHERCHE SCIENTIFIQUE, Paris (FR)

(72) Inventors: Pierre Guillot, Pessac (FR); Max Chabert, Bordeaux (FR); Annie Colin, Bordeaux (FR); Emmanuel Mignard, Paris (FR); Samuel Marre, Paris (FR); Cyril Aymonier, Paris (FR)

(73) Assignees: CENTRE NATIONAL DE LA RECHERCHE SCIENTIFIQUE, Paris (FR); RHODIA OPERATIONS, Auber Villiers (FR)

( * ) Notice: Subject to any disclaimer, the term of this patent is extended or adjusted under 35 U.S.C. 154(b) by 249 days.

(21) Appl. No.: 14/346,474

(22) PCT Filed: Sep. 21, 2012

(86) PCT No.: PCT/EP2012/068677
§ 371 (c)(1),
(2) Date: Mar. 21, 2014

(87) PCT Pub. No.: WO2013/041690
PCT Pub. Date: Mar. 28, 2013

(65) Prior Publication Data
US 2014/0238117 A1    Aug. 28, 2014

(51) Int. Cl.
*G01N 13/02*   (2006.01)

(52) U.S. Cl.
CPC ....... *G01N 13/02* (2013.01); *G01N 2013/0216* (2013.01); *G01N 2013/0283* (2013.01)

(58) Field of Classification Search
None
See application file for complete search history.

(56) References Cited

U.S. PATENT DOCUMENTS

| | | | |
|---|---|---|---|
| 3,030,802 A | 4/1962 | Aarts et al. | |
| 4,874,426 A | 10/1989 | Honda | |
| 5,559,284 A | 9/1996 | Matta et al. | |
| 8,613,217 B2 * | 12/2013 | Colin | G01N 13/02 73/64.48 |

(Continued)

FOREIGN PATENT DOCUMENTS

| | | |
|---|---|---|
| GB | 1317200 A | 5/1973 |
| GB | 2408572 A | 6/2005 |
| WO | WO 2009125119 A1 | 10/2009 |

OTHER PUBLICATIONS

Guillot, Pierre, et al—"Stability of a Jet in Confined Pressure-Driven Biphasic Flows at Low Reynolds Numbers", Sep. 2007, Physical Review Letters, PRL 99, 104502, The American Physical Society, DOI: 10.1103/PhysRevLett.99.104502, pp. 104502-1-104502-4; 4 pgs.

(Continued)

*Primary Examiner* — Paul West
*Assistant Examiner* — Mark A Shabman
(74) *Attorney, Agent, or Firm* — Vorys, Sater, Seymour and Pease LLP (57) ABSTRACT

The invention concerns a method whereby: (E1) an inner liquid phase is made to flow in an inner flow member, and an outer liquid phase in an outer flow member, the flow of the inner liquid phase opening within the flow of the second liquid phase; and the temperature and pressure in the contact area between the first and second liquid phases being such that the first and/or second liquid phase is in the supercritical state, (E2) the flow rate of the inner phase and/or outer phase is varied in such a way as to modify the flow profile, and a torque is identified from values of the flow rates of the inner and outer phases, called transition flow rates, from which the modification in the flow profile occurs (from drops to a jet; or from a jet to drops); (E3) from the transition torque identified in step (E2), the value of the interfacial tension between the two inner and outer liquid phases is calculated, or the result obtained is compared to that obtained for another torque in the conditions of steps (E1) and (E2).

20 Claims, 4 Drawing Sheets

(56) References Cited

U.S. PATENT DOCUMENTS

| | | | |
|---|---|---|---|
| 2003/0205079 A1 | 11/2003 | Taylor | |
| 2010/0116511 A1* | 5/2010 | Ramakrishnan | E21B 41/0064 166/400 |
| 2011/0197664 A1 | 8/2011 | Colin et al. | |
| 2011/0285042 A1* | 11/2011 | Viovy | B01J 13/04 264/4.3 |

OTHER PUBLICATIONS

Utada, Andrew S., et al—"Absolute Instability of a Liquid Jet in a Coflowing Stream", Jan. 2008, Physical Review Letters, PRL 100, 014502, The American Physical Society, DOI: 10.1103/PhysRevLett.100.014502; pp. 014502-1-014502-4; 4 pgs.

Ronay, Maria—"Determination of the Dynamic Surface Tension of Inks from the Capillary Instability of Jets" 1978, Journal of Colloid and Interface Science, vol. 66, Issue No. 1, pp. 55-67; 13 pgs.

Masayuki, Sato, et al—"Surface Tension Reduction of Liquid by Applied Electric Field Using Vibrating Jet Method", 1998, IEEE Transactions on Industry Applications, vol. 34, Issue No. 2, Mar./Apr. 1998, pp. 294-300; 7 pgs.

Adkins, Stephanie S., et al—"Effect of branching on the interfacial properties of nonionic hydrocarbon surfactants at the air-water and carbon dioxide-water interfaces", 2010, Journal of Colloid and Interface Science, vol. 346, pp. 455-463; 9 pgs.

U.S. Appl. No. 12/934,023, Annie Colin, et al, Nov. 16, 2010.

* cited by examiner

DETERMINATION OF INTERFACIAL TENSIONS IN SUPERCRITICAL CONDITIONS

CROSS-REFERENCE TO RELATED APPLICATIONS

This application is a U.S. national stage entry under 35 U.S.C. §371 of International Application No. PCT/EP2012/068677 filed Sep. 21, 2012, which claims priority to French Application No. 1102901 filed on Sep. 23, 2011, the whole content of these applications being incorporated herein by reference for all purposes.

TECHNICAL FIELD

The present invention deals with a method for determining the interfacial tension existing between two fluid phases, under temperature and pressure conditions in which at least one of the two fluid phases is in the supercritical state (the two fluid phases being able for example to be an aqueous phase and a phase based on $CO_2$ in the supercritical state). The invention also relates to devices suitable for the implementation of this method, as well as a screening procedure comprising one or more steps of measuring interfacial tensions under supercritical conditions employing the aforementioned determining method.

BACKGROUND ART

For the purposes of conciseness, in the subsequent description, the temperature and pressure conditions under which one and/or the other of two fluid phases present is in the supercritical state will be referred to by the generic term "supercritical conditions". Thus, two fluid phases termed "in supercritical conditions" or "under supercritical conditions" in the present description comprise (1) a first phase in the supercritical state and (2) a second phase, in contact with the first, and where said second phase is in the liquid, gaseous or supercritical state (generally liquid or gaseous). Two fluid phases termed "under supercritical conditions" according to the present description are therefore not necessarily both in the supercritical state. Stated otherwise, two phases having critical temperatures of T1 and T2 and critical pressures P1 and P2 respectively, the phases will be considered to be "under supercritical conditions" within the meaning of the present description if, and only if:
- the temperature is greater than T1 and the pressure is greater than P1; and/or
- the temperature is greater than T2 and the pressure is greater than P2.

The aforementioned interfacial tension under supercritical conditions exists between two non-miscible fluid phases under the supercritical conditions of measurement. Unless explicitly specified to the contrary, the expression "non-miscible fluid phases" refers, in the present description, to two phases in the liquid, gaseous or supercritical state and which are not miscible under the conditions of implementation of the method (it being understood that the two phases could optionally be miscible under other conditions).

Access to the knowledge of the value of interfacial tensions between two fluid phases under supercritical conditions is of importance, in numerous technological sectors. This parameter may indeed turn out to be critical in particular in certain physico/chemical methods employing a phase in the supercritical state, or else liable to lead in the course of their implementation to supercritical conditions. Inter alia, access to the value of the interfacial tension is of interest for processes employing $CO_2$ in the supercritical state, which can be used for example in syntheses or methods not employing any organic solvents; in petroleum recovery methods; or else for the capture and storage of $CO_2$.

The determination of an interfacial tension between two fluid phases under supercritical conditions is known as being relatively complex to implement. In fact, it generally requires heavyweight apparatus, in particular having regard to the high pressures which are employed. Moreover the procedures which have been proposed to date for the measurement of interfacial tensions in a supercritical medium generally involve long durations of measurement, as well as relatively significant volumes, with associated risks for the operators (supercritical conditions involving risks of explosion or of leakages which increase with the duration and the quantities). In addition to these safety problems, the proposed methods are often limited to the analysis of certain specific fluids and the conditions of analysis have to be adapted for each fluid pair studied.

The scant procedures which have currently been proposed for the measurement of interfacial tensions under supercritical conditions, prone to the aforementioned drawbacks, typically implement high-pressure visualization cells, within which the interfacial tension is determined according to the so-called "pending drop" (or "hanging drop") technique, where the measurement is performed by analyzing the shape adopted by a drop of a dense phase suspended within a less dense phase. For further details in this regard, reference may in particular be made to U.S. Pat. No. 5,653,250 or else to the article by Adkins et al. In the *Journal of Colloid and Interface Science*, vol. 346, p. 455 (2010).

SUMMARY OF THE INVENTION

An aim of the present invention is to provide a procedure making it possible to determine the interfacial tension between two fluid phases under supercritical conditions, while circumventing the aforementioned problems encountered with the procedures described hitherto. The invention is in particular aimed at providing a procedure making it possible to determine, in a manner which is at one and the same time reliable, simple and as inexpensive as possible, the value of interfacial tension between two fluid phases under supercritical conditions.

For this purpose, the present invention proposes a procedure in which the two fluid phases are made to flow under supercritical conditions in contact with one another, in co-current and typically with a coaxial flow, within a flow system of small dimensions, and where the nature of the flow obtained for various flow rates of the two fluid phases is observed. As a function of the respective flow rates of the two fluid phases, the co-current flow takes place either in the form of a continuous jet of one of the fluid phases within the other (for certain flow rate pairs), or in the form of drops of one of the fluid phases within the other (for the other pairs of flow rates). According to the procedure of the invention, the interfacial tension is determined by establishing at least one limit value of flow rate where the transition between the jet flow and the flow of drop type takes place (jet/drop transition).

More precisely, according to a first aspect the subject of the invention is a method for determining at least one value of interfacial tension between two non-miscible fluid phases, under supercritical conditions, which comprises the following successive steps:

(E1) a first fluid phase, termed the inner phase, is made to flow in a first, so-called inner, flow member with a first flow rate termed D1, and a second fluid phase, termed the outer phase, is made to flow in a second, so-called outer, flow member with a second flow rate termed D2 where the flux of the first fluid phase conveyed by the inner member discharges through an exit of the first flow member into the internal volume of the outer flow member within the flux of the second fluid phase; and the temperature and the pressure in the zone of contact between the first and the second fluid phase are such that at least the first and/or the second fluid phase is in the supercritical state, whereby, there is formed, downstream of the discharge of the inner flow member into the outer flow member, as a function of the respective values of the flow rates D1 and D2 and of their ratio:

EITHER drops of the inner phase in the outer phase;

OR a continuous jet of the inner phase in the outer phase;

and then (E2) the flow rate of the inner phase and/or of the outer phase is varied so as to modify the flow profile, namely:

IN THE CASE WHERE THE FLOW RATES D1 AND D2 STEP (E1) LEAD TO DROPS OF THE INNER PHASE IN THE OUTER PHASE: the flow rate of the inner phase and/or of the outer phase is modified until the formation of a continuous jet of the inner phase in the outer phase is obtained; and IN THE CASE WHERE THE FLOW RATES D1 AND D2 STEP (E1) LEAD TO A JET OF THE INNER PHASE IN THE OUTER PHASE: the flow rate of the inner phase and/or of the outer phase is modified until the formation of drops of the inner phase in the outer phase is obtained;

and a so-called transition pair of values of the flow rates of the inner and outer phases is identified, on the basis of which the modification of the flow profile takes place (from drops to jet or from jet to drops);

and then (E3) on the basis of the transition pair identified in step (E2), the value of interfacial tension between the two fluid phases, inner and outer, is calculated;

or else the transition pair obtained in step (E2) is compared with the transition pair for another system of fluid phases in the critical phase determined under the same conditions, whereby a relative indication between the values of interfacial tension of the two systems is obtained.

The two phases placed in presence in the aforementioned steps (E1) and (E2) are non-miscible: this term is understood in its broadest acceptation in the present description, namely that it refers to two fluids suitable for forming, by mixing, a two-phase system under the conditions implemented, and making it possible to observe the jet/drop transition defined hereinabove.

The implementation of steps (E1) to (E3) hereinabove turns out to be particularly easy, and it makes it possible in particular to carry out, at lesser cost and in a reduced time, reliable and reproducible measurements of the interfacial tensions between various fluids under supercritical conditions.

Moreover, in the most general case, the flow devices to be employed in steps (E1) and (E2) exhibit another advantage, namely that of not requiring any particular technical complexity. In particular, although more elaborate embodiments are conceivable, the inner and outer flow members employed according to the invention can typically be reduced to two coaxial cylindrical tubes. Alternatively, it may involve micro- or milli-fluidic chips, advantageously of glass or glass/silicon.

Furthermore, and more fundamentally, steps (E1) and (E2) turn out to be suitable for an implementation within flow devices of small dimensions, typically within coaxial capillary tubes. Thus, the inner and outer flow members employed according to the invention can be two coaxial capillary tubes, thereby making it possible in particular to reduce the quantities of phases placed in presence under supercritical conditions, this being manifested, inter alia, in terms of speed of data acquisition and of decreased risks related to the implementation of supercritical conditions.

According to one interesting embodiment where the possibility of reducing the size of the device is well exploited, the outer diameter of the inner flow member is between 10 micrometers and 2 millimeters, for example between 20 and 200 micrometers. The inner diameter of the outer flow member can for its part advantageously be between 50 micrometers and 4 millimeters, for example between 100 and 500 micrometers, it being understood that, by definition, this inner diameter of the outer flow member remains greater than that of the outer diameter of the inner flow member. The difference between the inner diameter of the outer flow member and outer diameter of the inner flow member remains preferably between 5 micrometers and 2 millimeters, for example between 10 and 500 micrometers, and a ratio of the inner diameter of the outer flow member to the outer diameter of the inner flow member is between 1.1 and 10, preferably between 1.3 and 5.

The nature of the flow members employed according to the invention has to be adapted to the implementation of the supercritical conditions of steps (E1) and (E2). In most cases, and in particular when steps (E1) and (E2) implement $CO_2$ in the supercritical state, it is possible to use by way of flow members capillary tubes based on fused silica, which make it possible to achieve flows under pressures exceeding 75 bars and typically of up to at least 100 bars or indeed up to 200 bars. Advantageously, according to an embodiment which corresponds to that of the here-appended example, the inner and outer flow members are polyimide-sheathed fused silica capillaries, connected by connection technology elements consisting of PEEK (polyether ethyl ketone) plastic. Particularly well-suited flow members are for example the capillary tubes of the type of those marketed by the company Polymicro Technologies under the name "Flexible Fused silica capillary tubing".

In particular when the flow devices exhibit reduced dimensions, for example with diameters in the aforementioned ranges, each of the flow rates of the fluid phases within the flow members in steps (E1) and (E2), and in particular each of the flow rates D1 and D2 of step (E1) can preferably be between 10 microliters per hour and 1000 ml per hour, preferably between 100 microliters per hour and 100 ml per hour.

In practice, whatever the dimensions of the device employed, the experimental conditions of step (E1) and of step (E2) may advantageously be identical, with the exception of the values of the flow rates of the fluid phases.

According to an interesting embodiment of steps (E1) and (E2), the so-called outer flow rate of the outer fluid phase can be held fixed (at the value D2) in steps (E1) and (E2), whilst solely the so-called inner flow rate of the inner fluid phase is varied in step (E2). Conversely, according to another possible embodiment, it is the inner flow rate which can be held fixed (at the value D1), whilst the outer flow rate is variable in step (E2). Alternatively, according to another conceivable although trickier mode, it is possible to vary the two flow rates jointly, simultaneously or not, in step (E2).

The identification of the nature of the flow in steps (E1) and (E2), namely the existence of drops or of a jet, can typically be carried out by employing an outer flow member which is at least locally transparent for a laser radiation on at least one portion of the outer flow member, said portion being situated downstream of the discharge of the inner flow member into the outer flow member. To identify the nature of the flow, this transparent zone of the flow member is placed between an emitter of said laser radiation and a receiver of said laser radiation (typically a photodiode), thus leading to two types of signals received by the receiver making it possible to distinguish the two types of flow, namely (i) a substantially continuous signal in the case of a jet (the laser beam is permanently crossed by a phase of like type); and (ii) a discontinuous signal in the case of the drops (the laser beam is crossed in succession by drops of the internal phase and then by the external carrier phase between the traversal of each drop).

The determination of the value of the interfacial tension in step (E3) can for its part be carried out according to any suitable procedure adapted on the basis of the knowledge of the pair of transition flow rates which is established in step (E2) and of the physical characteristics of the flow devices employed and of the fluid phases present.

Thus, for example, when steps (E1) and (E2) are carried out with a flow rate of the outer fluid phase fixed at the value of D2, the value of the interfacial tension can be established on the basis of the transition flow rate of the inner fluid phase, of the inner diameter of the outer flow member, and of the viscosities of the inner and outer fluid phases, typically by employing the following equation:

$$Kax^3 E(x, \lambda) = CF(x, \lambda) \text{ where}$$

$$C = \frac{5 + \sqrt{7}}{18} \sqrt{\frac{24}{\sqrt{7} - 1}},$$

$$E(x, \lambda) = -4x + (8 - 4\lambda^{-1})x^3 + 4(\lambda^{-1} - 1)x^3,$$

$$F(x, \lambda) =$$
$$x^4(4 - \lambda^{-1} + 4\ln(x)) + x^6(-8 + 4\lambda^{-1}) + x^8(4 - 3\lambda^{-1} - (4 - 4\lambda^{-1})\ln(x)),$$

$$\lambda = \frac{\eta_i}{\eta_e},$$

$$\alpha = \sqrt{\left(1 + \lambda^{-1} \frac{Qi}{Qe}\right)},$$

$$x = \frac{2rj}{De} = \sqrt{\frac{\alpha - 1}{\lambda^{-1} + \alpha - 1}},$$

$$Ka = \frac{\Delta P D_e^2}{4L\gamma}, \text{ with}$$

$$\frac{\Delta P}{L} = \frac{128 \eta_e Q_e}{\pi D_e^4 (1 - x^2)} \text{ the pressure gradient}$$

According to an embodiment making it possible to further refine the measurement of the interfacial tension, the value of the interfacial tension between two like fluid phases under the same supercritical conditions can be determined several times in succession, for example by carrying out steps (E1) to (E3) several times at fixed outer flow rate and by varying the inner flow rate in step (E2), and by fixing at each cycle of step (E1) to (E3) a distinct value for the outer flow rate (namely with a flow rate D2 for the first cycle, a flow rate D'2≠D2 for the second cycle, a flow rate D"2 also distinct from D2 and D'2 in the case of a third cycle, etc.).

It should be noted that, on account of its great simplicity of implementation, the method of the invention exhibits very great modularity and can be implemented in a very great number of applications. The method makes it possible in particular to carry out with a high acquisition rate successive measurements relating to phases of distinct natures without having to adapt the experimental conditions and the measurement conditions between each of the acquisitions.

In contradistinction to the techniques proposed hitherto, the procedure proposed according to the present invention makes it possible furthermore to determine the value of the interfacial tension of a very great number of pairs of fluid phases, without having to adapt case by case the nature of the analysis to be carried out when the physical or chemical nature of one and/or of the other of the fluid phases is modified. It can moreover be carried out according to a continuous mode and the nature of one and or the other of the two phases can be modified over time during this continuous process, thereby exhibiting a further advantage of the method.

According to a very particular embodiment, the placing in contact of the fluid phases in steps (E1) and (E2) is carried out in the presence of a surfactant. In this case, steps (E1) to (E3) can typically be implemented several times in succession under similar conditions but with variable quantities of surfactant, making it possible to vary the drop formation time, and to determine, on the basis of a curve of the evolution of the interfacial tension value as a function of the drop formation time, a characteristic time of the surfactant, corresponding to the transition between a zone where the interfacial tension value remains substantially constant as a function of the formation time, and an adjacent zone, where this interfacial tension value increases as this formation time decreases.

The method of the invention can be employed to determine the interfacial tension existing between two fluid phases in any physico/chemical method employing a phase in the supercritical state, or else liable to lead in the course of their implementation to supercritical conditions. In this case, the first fluid phase comprises supercritical $CO_2$ or another fluid in the supercritical state. It can in particular be used to measure the interfacial tension in processes employing $CO_2$ in the supercritical state or any other supercritical fluid, for example in synthesis reactions carried out in emulsion in supercritical $CO_2$; in methods of extraction using supercritical $CO_2$ including in particular petroleum recovery methods; or else in methods for capturing and storing $CO_2$ where the $CO_2$ is employed in the supercritical state.

According to another aspect, the subject of the present invention is also an installation suitable for the implementation of the aforementioned method comprising steps (E1) to (E3). This installation typically comprises:

an inner flow member and an outer flow member, which are preferably coaxial, the inner flow member discharging into the internal volume of the outer flow member;

means for feeding with two fluid phases, respectively in the two flow members, suitable for conditions where one of the phases is in the supercritical state;

means for controlling the temperature and pressure within the installation, suitable for bringing at least the internal space of the outer flow member into supercritical conditions of temperature and pressure for at least one of the fluid phases;

means for varying the flow rate of at least one of the fluid phases; and means for observing the nature of the flow downstream of the discharge of the inner flow member into the outer flow member.

According to yet another aspect, the subject of the invention is finally a method for screening various pairs of fluid phases, in which these various pairs are prepared, at least one value of interfacial tension relating to each of these pairs is determined, according to the aforementioned steps (E1) to (E3), and at least one preferred pair is identified, from among said several screened pairs.

According to a particular mode of implementation, this mode of screening is employed by conducting steps (E1) and (E2) in succession, under the same conditions, firstly with a first pair of fluid phases, and then for a second pair of fluid phases, and then by comparing in step (E3) the results obtained in the two cases, whereby the two pairs are compared the one with respect to the other.

This screening method is in particular suitable for the implementation of the following variants:

it is possible to prepare the various pairs by adding at least one substance to at least one of the phases, for example a surfactant and/or a polymer and/or a solid particle and/or a mixture of several compounds, for example an oil or crude petroleum; and it is possible to prepare the various pairs by modifying at least one condition of at least one phase, for example its pH.

According to a particular embodiment of the screening method of the invention, at least one of the pairs employed comprises crude petroleum, preferably within supercritical $CO_2$.

BRIEF DESCRIPTION OF DRAWINGS

The invention will now be described in greater detail hereinafter, with reference to the appended drawings and to the example hereinafter, where.

DETAILED DESCRIPTION OF THE INVENTION

Figure 1:
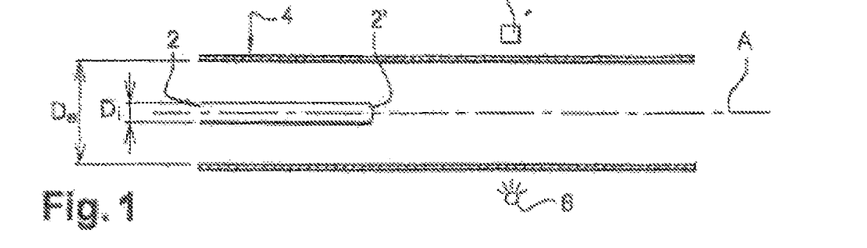
FIG. 1 is a side view, illustrating an installation allowing the implementation of a method for determining the interfacial tension between two fluid phases, in accordance with the invention.

In FIG. 1, there is illustrated an installation in accordance with the invention, which comprises two flow members, respectively an inner flow member 2 and an outer flow member 4. In this illustrative example, these flow members 2 and 4 are capillaries, made in particular of fused silica, knowing that other flow members are conceivable.

The two capillaries 2 and 4 illustrated in the figure are coaxial, and thus possess a common main axis, denoted A. Moreover $D_i$ refers to the external diameter of the inner capillary 2, namely that this diameter includes the walls of the capillaries. Furthermore $D_e$ denotes the internal diameter of the outer capillary 4, namely that conversely this value of diameter does not include the walls of this capillary 4.

In an advantageous manner, $D_i$ is between 10 microns (or micrometers) and 2 millimeters, preferably between 10 microns and 200 microns, whilst $D_e$ is between 50 microns and 4 millimeters, preferably between 100 microns and 500 microns. Furthermore, the ratio $D_e/D_i$ is advantageously between 1.1 and 10, preferably between 1.3 and 5.

The discharge of the inner capillary 2, in the internal volume of the outer capillary 4, is denoted 2'. Immediately downstream of this discharge 2', there is provided a laser emitter 6, on a first side of the capillary 4, which is associated with a photodiode 8, placed opposite this emitter 6. This emitter and this photodiode are able to deliver a signal, making it possible to obtain information on the formation of drops as well as on the frequency of this formation.

Figure 8:
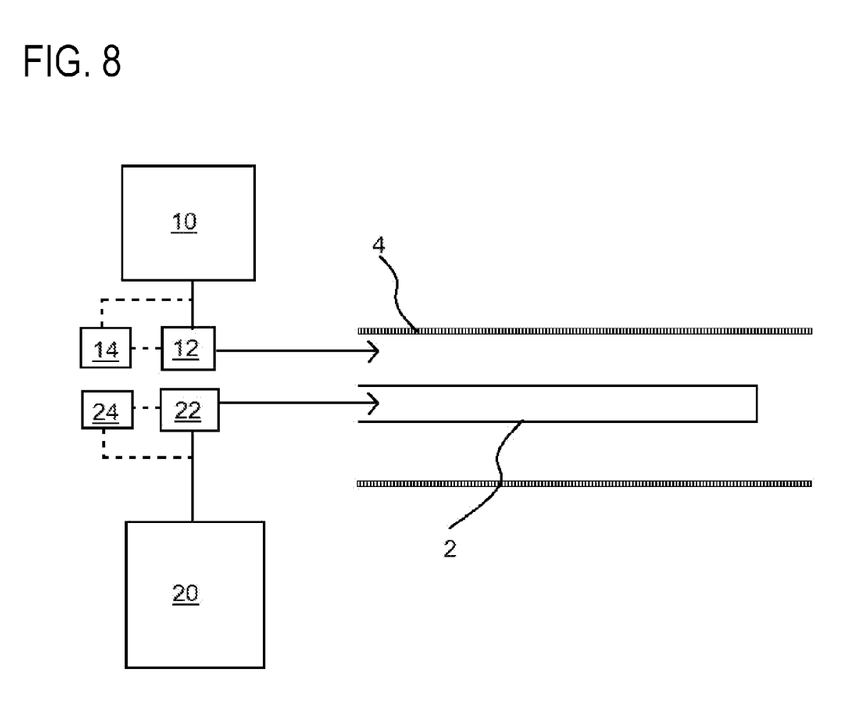
FIG. 8 is the side view of FIG. 1 modified to add feeders and controllers.

The installation described hereinabove, with reference to FIG. 1, allows the implementation of a method in accordance with the invention, aimed at determining the interfacial tension between two fluid phases. For this purpose, the capillaries 2 and 4 are placed in communication with means of supply of two non-miscible phases to be tested. These supply means, which are of conventional type, are not represented in the FIGS. 1-5, but are shown as feeders 10, 20 in FIG. 8, wherein feeder 10 is employed with flow controller 12 and temperature and pressure controller 14 and feeder 20 is employed with flow controller 22 and temperature and pressure controller 24. In a customary manner, this may for example entail syringe plungers and microfluidic connection technologies.

According to a possible embodiment, illustrated in the figures, the outer flow rate, denoted $Q_e(1)$, of the fluid phase (Le) flowing in the outer capillary is fixed. In an advantageous manner, this outer flow rate value is between 10 microliters/hour and 1000 ml/hour, preferably between 100 microliters/hour and 100 ml/hour. Moreover, very low values are given to the inner flow rate, denoted $Q_i$, of the fluid phase (Li) flowing in the inner capillary and to the outer flow rate $Q_e$ of the fluid phase (Le) flowing in the outer capillary. Under these conditions, the placing in contact of these two non-miscible fluid phases leads to the formation of drops G which consist of the inner fluid phase, in a carrier phase P formed by the outer fluid phase (see FIG. 2).

Figure 2:
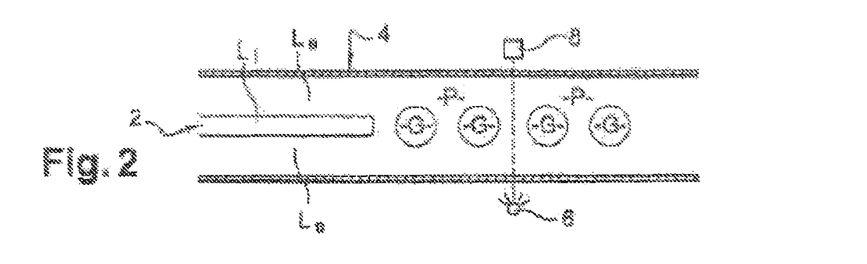
FIGS. 2, 4 and 5 are side views, analogous to FIG. 1, illustrating various steps for implementing this method.

Next, for this same outer flow rate $Q_e(1)$, the value of the flow rate $Q_i$, is increased progressively according to a predetermined time-dependent function $Q_i=f(t)$. The signal emitted by the photodiode is then observed, as a function of time.

Figure 3:
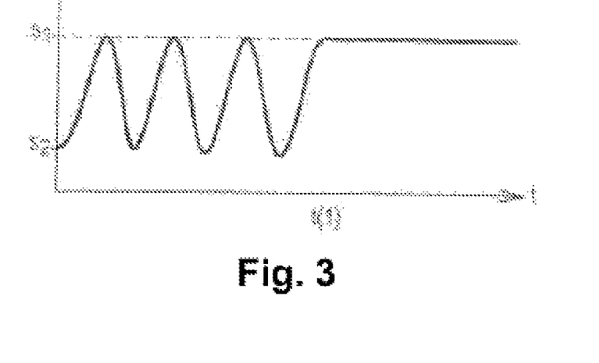
FIG. 3 is a graph, illustrating the variations of the signal of a photodiode as a function of time.
Figure 4:
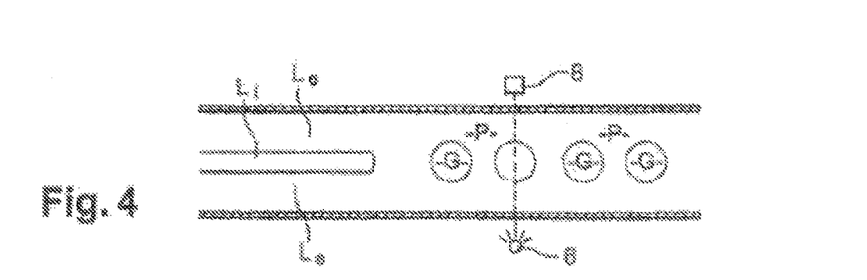

At the start of the flow of the two fluid phases, corresponding to the formation of drops, the signal is periodic, namely it oscillates between two values, respectively $s_1$ and $s_2$ (see FIG. 3). The value $s_1$ corresponds to the position, in which the laser and the photodiode are separated both by the inner fluid phase and the outer fluid phase (FIG. 4), whilst the signal $s_2$ corresponds to the position, for which this laser and this photodiode are separated solely by the outer fluid phase (FIG. 2).

Figure 5:
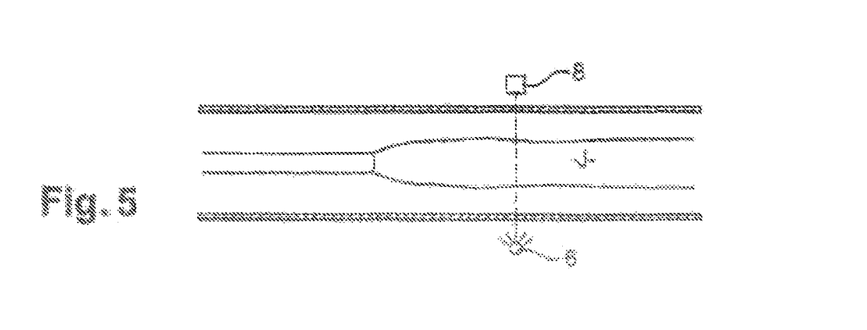

Above a certain flow rate value $Q_i$, it is noted that the drops initially produced are replaced by a continuous jet J of the inner fluid phase in the outer fluid phase (FIG. 5). From the moment this threshold value is attained, the signal emitted by the photodiode stabilizes at the value $s_1$, since the laser and the photodiode are permanently separated both by the inner fluid phase and by the outer fluid phase.

The instant, denoted t(1), corresponding to the appearance of the continuous jet is identified on the basis of the curve of FIG. 3. Given that, as seen hereinabove, the variation in flow rate $Q_i$ is known as a function of time, it is possible to ascertain the flow rate value $Q_i(\mathbf{1})$ corresponding to this instant t(1) of formation of the jet. Knowing the value of the outer flow rate $Q_e(\mathbf{1})$, as well as the value of the internal flow rate $Q_i(\mathbf{1})$ for which the continuous jet appears, it is possible to deduce therefrom the value of the interfacial tension $\gamma(\mathbf{1})$ between the two fluid phases.

For this purpose, the following equation is used:

$$Ka\alpha^3 E(x, \lambda) = CF(x, \lambda) \text{ where}$$

$$C = \frac{5+\sqrt{7}}{18}\sqrt{\frac{24}{\sqrt{7}-1}},$$

$$E(x, \lambda) = -4x + (8 - 4\lambda^{-1})x^3 + 4(\lambda^{-1} - 1)x^3,$$

$$F(x, \lambda) =$$
$$x^4(4 - \lambda^{-1} + 4\ln(x)) + x^6(-8 + 4\lambda^{-1}) + x^8(4 - 3\lambda^{-1} - (4 - 4\lambda^{-1})\ln(x)),$$

$$\lambda = \frac{\eta_i}{\eta_e},$$

$$\alpha = \sqrt{\left(1 + \lambda^{-1}\frac{Qi}{Qe}\right)}, \text{ and}$$

$$x = \frac{2rj}{De} = \sqrt{\frac{\alpha - 1}{\lambda^{-1} + \alpha - 1}}.$$

Solving equation (1) hereinabove makes it possible to ascertain the value of Ka, and then that of $\gamma$ using the following equation:

$$Ka = \frac{\Delta P D_e^2}{4L\gamma}, \text{ with}$$

$$\frac{\Delta P}{L} = \frac{128\eta_e Q_e}{\pi D_e^4(1-x^2)} \text{ the pressure gradient}$$

As is apparent from the foregoing, it is possible to deduce this interfacial tension value by knowing solely the values of the fixed outer fluid phase flow rate Qe, of the transition inner fluid phase flow rate Qi, of the diameter De of the outer capillary, as well as of the viscosities $\eta_i$ and $\eta_e$ of the inner and outer fluid phases. This value can therefore be known in a simple and fast manner.

It is possible to repeat the operation described hereinabove, fixing the external flow rate $Q_e$ at different values, denoted $Q_e(\mathbf{2})$ to $Q_2(n)$, each time. This makes it possible to ascertain corresponding values of internal flow rate, denoted $Q_i(\mathbf{2})$ to $Q_i(n)$, for which the transition between the drops and the jet takes place. For each group of values $Q_i(j)$ and $Q_e(j)$, where j varies from 1 to n, it is also possible to deduce n interfacial tension values denoted $\gamma(\mathbf{1})$ to $\gamma(n)$. The values of inner flow rate $Q_i$ are typically between 10 microliters/hour and 1000 ml/hour, in particular between 100 microliters/hour and 100 ml/hour.

By way of variant, for a fixed outer flow rate, it is possible to choose a very high initial value of inner flow rate, such that the placing in contact of the two fluid phases leads to the formation of a jet.

Thereafter, this inner flow rate value is decreased progressively until drops are obtained. In a manner similar to what was described hereinabove, the inner flow rate sought corresponds to that for which the transition between jet and drops is identified, and not between drops and jet as in the first embodiment illustrated in FIG. 2.

By way of variant, it is possible to envision fixing, not the outer flow rate, but the inner flow rate so that, in this case, the outer flow rate is then varied. This may be beneficial for reducing the errors in the measurements, in particular by carrying out firstly a first series of measurements with fixed outer flow rate, and then a second series with fixed inner flow rate, for the same fluid phases. It is then possible, in an advantageous manner, to average the values obtained during these two series of measurements.

According to an advantageous variant of the invention, it is possible to carry out a screening of various pairs of fluid phases, by using the method for determining surface tension, such as described hereinabove.

For this purpose, the flow capillaries 2 and 4 are linked up with means for adding at least one substance to at least one fluid phase, and/or with means making it possible to modify the conditions of the flow of at least one of these fluid phases. The adding means make it possible to add, to one and/or the other of the fluid phases, various types of substances such as a surfactant, a polymer, solid particles, salts, acids, or bases or mixtures of one or more substances, for example of crude petroleum or an oil. The means for modifying the flow conditions are for example able to vary the pH, the temperature, or else the pressure.

A pair of so-called base fluid phases is thereafter prepared, whose surface tension is determined in accordance with the method described hereinabove. Next, the base pair is modified, by adding at least one substance to at least one fluid phase, and/or modifying at least one condition of at least one of these base fluid phases.

The various surface tensions, relating to the various fluid phase pairs thus prepared, are then determined. Finally, one or more preferred fluid phase pairs is or are determined, for example those exhibiting the lowest surface tension.

According to the invention, it is possible to measure various values of interfacial tension as a function of the rate of formation of the drops, thereby making it possible to determine the rate of adsorption of a surfactant at the interface between the fluid phases, namely the dynamic interfacial tension. Accordingly, use is made of the installation described previously and a surfactant agent, whose properties it is desired to determine, is introduced into the flowing phases. This surfactant is added, in a customary manner, to one and/or the other of the fluid phases.

An illustrative mode of implementation of the procedure usable to determine the properties of a surfactant according to the invention will now be described in greater detail.

Typically, firstly in a first step, an outer flow rate $Q_e$ is fixed at a very low value, denoted $Q_e(\mathbf{1})$, thereby making it possible to ensure that the surfactant has the time required to be adsorbed at the interface between the two fluid phases, and then the inner fluid phase is made to flow at a very low initial flow rate, which is increased progressively according to the scheme described hereinabove. The inner flow rate value, beyond which the drops are transformed into a continuous jet, is denoted $Q_i(\mathbf{1})$. The frequency of formation of these drops is denoted $\omega_1$ which is very small on account of the very low flow rate value $Q_e(\mathbf{1})$. This frequency of formation is measured for example by the laser emitter 6, associated with the photodiode 8. Finally, the value γ1 of the interfacial tension is calculated according to the aforementioned equation, on the basis of the value $Q_e(1)$ and $Q_i(1)$ hereinabove.

In a second step, the outer flow rate is fixed at a value $Q_e(2)$ greater than that $Q_e(1)$ hereinabove. Consequently, the frequency $\omega_2$ of formation of the drops will be greater than that $\omega_1$, mentioned hereinabove. Next, in a manner analogous to the first step, the flow rate $Q_i$, is made to vary, until a value $Q_i(2)$ is identified corresponding to the transition between the drops and the continuous jet. This makes it possible to obtain a second value of interfacial tension, denoted γ2.

These two steps are thereafter repeated, in an iterative manner, for n flow rate values, thereby making it possible to obtain n values of frequency of formation of drops, as well as n values of interfacial tension.

The curve obtained for the variation of the interfacial tension γ as a function of the drop formation time t, which corresponds to the inverse of the frequency ω, typically divides into two main zones, namely:

- a first zone I, corresponding to high formation times and consequently to low production frequencies, for which the value of the interfacial tension γ is substantially constant. Stated otherwise, in this portion of curve, the drops form slowly enough to allow the surfactant to be adsorbed at the interface between the two fluid phases.
- a second zone II, corresponding to higher formation frequencies, namely shorter formation times. As the minimum formation time $t_n$ is approached, an increase in the interfacial tension γ is noted. Stated otherwise, the more the drops form at high frequencies, the less time the surfactant has to be adsorbed and, consequently, the more the interfacial tension increases.

At the intersection between the zones I and II, a transition point corresponds to the minimum characteristic time denoted $t_K$, required for the adsorption of the surfactant at the interface between the two fluid phases. Stated otherwise, the time is a value characteristic of the surfactant studied, in the sense that it corresponds to the minimum duration required for this surfactant to be adsorbed at the interface between the two fluid phases.

By using the procedure which has just been described, it is possible to implement a method for screening various surfactant agents. For this purpose, two base non-miscible fluid phases are used, which are made to flow in the capillaries 2 and 4. Next, various surfactant agents are added to them in succession, whose characteristic times $t_K$ are measured, according to the steps described hereinabove. The preferred surfactant agent or agents corresponds or correspond in particular to those whose characteristic times are less than the characteristic times of the application.

The invention will be yet further illustrated hereinafter, in the light of the exemplary embodiment which follows, where the procedure described hereinabove with reference to the figures has been implemented by using as immiscible fluid phases respectively liquid water and $CO_2$ in the supercritical state (implemented at a pressure of 165 bar ($165.10^5$ Pa) and at a temperature of 50° C., and as flow members two fused silica coaxial capillary tubes marketed by the company Polymicro Technologies under the name "Flexible Fused silica capillary tubing", having the following diameters respectively:

outer capillary: inner diameter: 250 microns
inner capillary: inner diameter: 100 microns
outer diameter: 150 microns

EXAMPLE

Determination of the Surface Tension in the Presence of Surfactant in a Water/Supercritical $CO_2$ Mixture Water and supercritical $CO_2$ were injected at co-current into the two flow members, under the aforementioned temperature and pressure conditions, while varying their respective flow rates. Supercritical $CO_2$ was injected through the internal capillary tube, within the liquid water conveyed by the external tube and playing the role of carrier phase.

Figure 6:
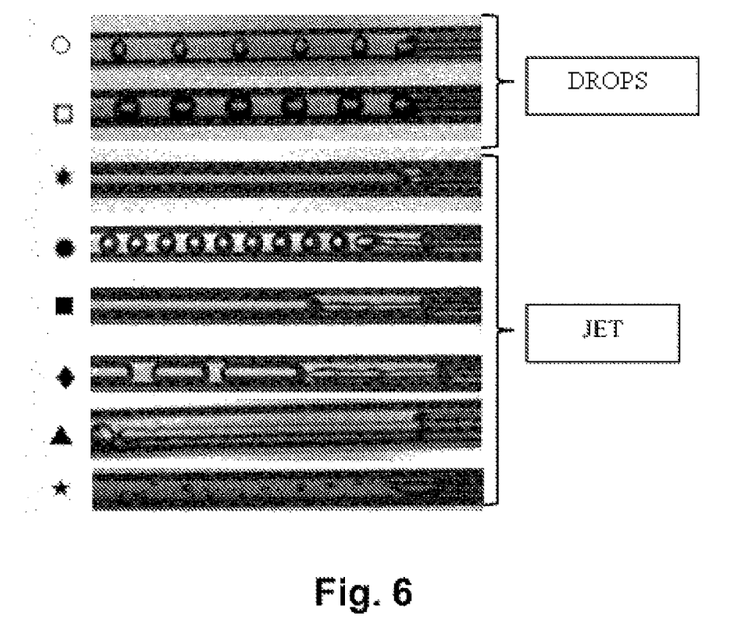
FIG. 6 represents various flow regimes of jet or drop type observed within the framework of the example.

As a function of the flow rates, various flow regimes are observed, namely a so-called jet regime (or 'Jetting'), where the supercritical $CO_2$ flows in the form of a jet on exiting the internal capillary, and a so-called drop regime (or 'Dripping'), where the $CO_2$ forms drops on exiting the internal capillary, as illustrated in the appended FIG. 6.

Figure 7:
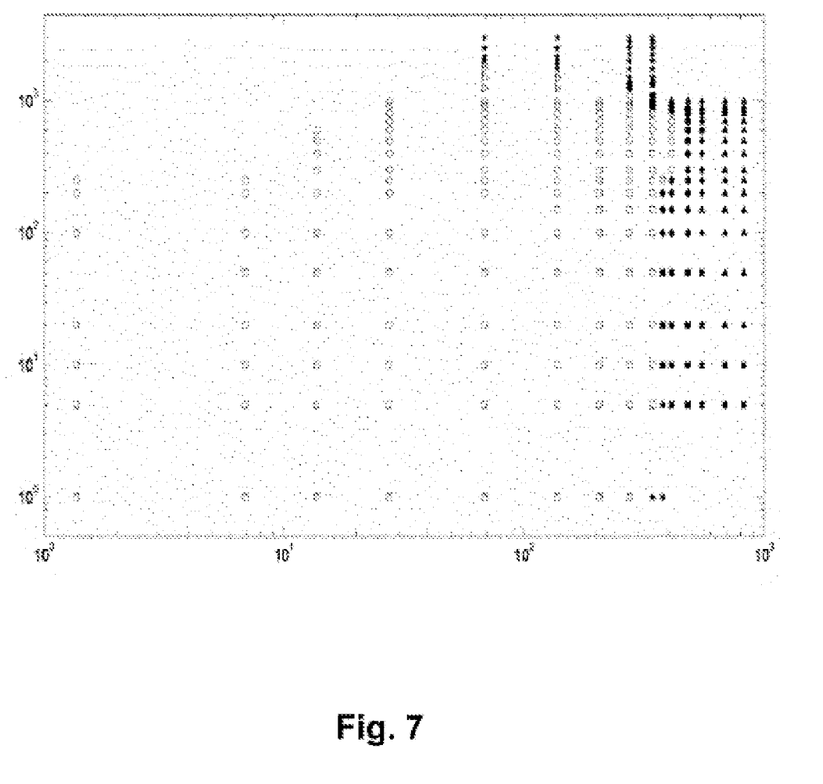
FIG. 7 is a phase diagram obtained within the framework of the example, showing the evolution of the flow regime under the effect of the variation of the flow rates.

Note that FIG. 6 is very illustrative of the notion of "drop" regime and "jet" regime such as it is employed in the present description. In this regard, it will be noted that the notion of drop or of jet within the meaning of the present invention is given with reference to the behavior at the level of the exit of the inner flow member. On the basis of the observation of the various regimes obtained, a dynamic phase diagram charting the nature of the regime as a function of the fluxes of the internal phase and of the external phase given as abscissa and as ordinate respectively, as illustrated in the appended FIG. 7.

Similar measurements were performed with various surfactants added to the medium, which modify the dynamic phase diagram obtained in the absence of surfactant.

A first surfactant employed within this framework was cetyl trimethylammonium bromide (CTAB), added in an amount of 2% by mass to the liquid aqueous phase.

The addition of this surfactant modifies the values of the flow rates leading to the jet/drop transition. The value of the surface tension does in fact decrease on account of the addition of the surfactant.

The procedure of the invention can be obtained so as to establish the complete phase diagram or else solely to determine the flow rates which lead to the transition.

On the basis of these flow rate values, with the aid of the aforementioned equations, it is possible to infer the value of the surface tension.

The procedure of the invention was also used to intercompare various solvents. For this purpose, it is possible to calculate the value of the surface tension for each of the solvents, but, more simply, within the framework of this example, the same conditions were simply retained while using various surfactants, thereby making it possible, by direct comparison and without calculation, to identify the effect of each of the surfactants employed.

The invention claimed is:

1. A method for determining at least one value of interfacial tension between two non-miscible fluid phases, under supercritical conditions, comprising the following successive steps:

(E1) flowing a first fluid phase, termed the inner phase, in a first inner flow member (2), with a first flow rate D1, and flowing a second outer fluid phase in a second outer flow member (4) with a second flow rate D2
wherein,
the flux of the first fluid phase conveyed by the inner member discharges through an exit of the first flow member into the internal volume of the outer flow member within the flux of the second fluid phase; and
the temperature and the pressure in the zone of contact between the first and the second fluid phase are such that at least the first and/or the second fluid phase is in the supercritical state,
wherein the inner flow member (2) and the outer flow member (4) are two coaxial capillary tubes,
wherein downstream of the discharge (2') of the inner flow member into the outer flow member, as a function of the respective values of the flow rate D1 of the inner phase and D2 of the outer phase and of their ratio, is formed a flow profile of:
either drops of the inner phase in the outer phase;
or a continuous jet of the inner phase in the outer phase; and then
(E2) varying the flow rate of the inner phase and/or of the outer phase to modify the flow profile, namely:
in the case where the flow rates D1 of the inner phase and D2 of the outer phase in said step (E1) lead to drops of the inner phase in the outer phase: modifying the flow rate of the inner phase and/or of the outer phase until the formation of a continuous jet of the inner phase in the outer phase is obtained; and
in the case where the flow rates D1 of the inner phase and D2 of the outer phase in said step (E1) lead to a jet of the inner phase in the outer phase: modifying the flow rate D1 of the inner phase and/or the flow rate D2 of the outer phase until the formation of drops of the inner phase in the outer phase is obtained;
and identifying a transition pair of values of the flow rate D1 of the inner and the flow rate D2 outer phases, on the basis of which the modifying of the flow profile takes place from drops to jet or from jet to drops;
and then
(E3) on the basis of the transition pair identified in said step (E2),
calculating the value of interfacial tension between the two fluid phases, inner and outer; or
comparing the transition pair obtained in said step (E2) with the transition pair for another system of fluid phases in the critical phase determined under the same conditions, to obtain a relative indication between the values of interfacial tension of the two systems.

2. The method as claimed in claim 1, wherein, in said step (E3), on the basis of the transition pair identified in said step (E2), the value of interfacial tension between the two fluid phases, inner and outer, is calculated.

3. The method as claimed in claim 1, wherein the inner flow member (2) and the outer flow member (4) are two coaxial capillary tubes, wherein an outer diameter of the inner capillary tube is between 10 micrometers and 2 millimeters and the inner diameter of the outer flow member is between 50 micrometers and 4 millimeters, and a ratio of the inner diameter of the outer flow member to the outer diameter of the inner flow member is between 1.1 and 10.

4. The method as claimed in claim 1, wherein the outer diameter of the inner flow member (2) is between 10 micrometers and 2 millimeters and the inner diameter of the outer flow member (4) is between 50 micrometers and 4 millimeters, wherein the inner diameter of the outer flow member remains greater than the outer diameter of the inner flow member.

5. The method as claimed in claim 1, wherein each said capillary comprises a tube of fused silica.

6. The method as claimed in claim 1, wherein the flow rate of the outer fluid phase is held fixed at the value D2 in said steps (E1) and (E2), whilst the flow rate of the inner fluid phase alone is varied in said step (E2).

7. The method as claimed in claim 1, wherein the flow rate of the inner fluid phase is held fixed at the value D1 in said steps (E1) and (E2), whilst the flow rate of the outer fluid phase alone is varied in said step (E2).

8. The method as claimed in claim 1, wherein the placing in contact of the fluid phases in said steps (E1) and (E2) is carried out in the presence of a surfactant.

9. The method as claimed claim 1, wherein said first fluid phase comprises supercritical $CO_2$.

10. An installation for the implementation of the method of claim 1 comprising:
an inner flow member and an outer flow member, wherein the inner flow member and the outer flow member are coaxial capillary tubes, the inner flow member located for discharging into the internal volume of the outer flow member;
a feeder for the first fluid phase and a feeder for the second fluid phase with the first and second fluid phases, respectively in the two flow members, suitable for conditions where one of the phases is in the supercritical state;
a temperature and pressure controller within the installation, for bringing at least the internal space of the outer flow member into supercritical conditions of temperature and pressure for at least one of the fluid phases;
a flow controller to vary the flow rate of at least one of the fluid phases; and
at least a portion of the outer tube being sufficiently transparent so the nature of the flow downstream of the discharge of the inner flow member into the outer flow member is observable.

11. The installation as claimed in claim 10, wherein the inner flow member (2) and the outer flow member (4) are two coaxial capillary tubes, wherein an outer diameter of the inner capillary tube is between 10 micrometers and 2 millimeters and the inner diameter of the outer flow member is between 50 micrometers and 4 millimeters, and a ratio of the inner diameter of the outer flow member to the outer diameter of the inner flow member is between 1.1 and 10.

12. The installation as claimed in claim 10, wherein at least one of the pairs employed comprises crude petroleum, within supercritical $CO_2$.

13. The method according to claim 1 wherein at least one of the pairs employed comprises crude petroleum.

14. The method according to claim 1, wherein at least one of the pairs employed comprises crude petroleum, within supercritical $CO_2$.

15. The method according to claim 14, wherein the capillary tubes are based on fused silica and the flow rates of the fluid phases in steps (E1) and (E2) are between 10 microliters per hour and 1000 ml per hour.

16. The method according to claim 1, wherein at least one of the pairs employed comprises crude petroleum, within supercritical $CO_2$, wherein the outer flow member is at least locally transparent for a laser radiation on at least one portion of the outer flow member, said portion of the outer flow member being downstream of the discharge end of the inner flow member into the outer flow member, to identify the nature of the flow, this transparent zone of the flow member is placed between an emitter of said laser radiation and a photodiode receiver of said laser radiation,     wherein the receiver distinguishes between two types of signals to distinguish the two types of flow selected from the group consisting of     (i) a substantially continuous signal in the case of a jet, of the first fluid phase conveyed by the inner member discharges through an exit of the first flow member into the internal volume of the outer flow member as an internal phase within the flux of the second fluid phase, wherein the laser beam is continuously crossed by the internal phase as a phase of like type; and     (ii) a discontinuous signal in the case of the drops, of the first fluid phase conveyed by the inner member discharges through an exit of the first flow member into the internal volume of the outer flow member as the internal phase within the flux of the second fluid phase which is an external carrier phase, wherein the laser beam is crossed in succession by drops of the internal phase and then by the external carrier phase between the traversal of each drop.

17. A method of screening of at least two distinct pairs of fluid phases, in which at least one value of interfacial tension relating to each of these pairs is determined according to steps (E1) to (E3), and at least one pair is identified, among several screened pairs, wherein     in said step (E1) flowing a first fluid phase, termed the inner phase, in a first inner flow member (2), with a first flow rate D1, and flowing a second outer fluid in a second outer flow member (4) with a second flow rate D2, wherein,         the flux of the first fluid phase conveyed by the inner member discharges through an exit of the first flow member into the internal volume of the outer flow member within the flux of the second fluid phase; and         the temperature and the pressure in the zone of contact between the first and the second fluid phase are such that at least the first and/or the second fluid phase is in the supercritical state,     wherein the inner flow member (2) and the outer flow member (4) are two coaxial capillary tubes,     wherein downstream of the discharge (2') of the inner flow member into the outer flow member, as a function of the respective values of the flow rate D1 and D2 and of their ratio, is formed:

either drops of the inner phase in the outer phase;

or a continuous jet of the inner phase in the outer phase,     in said step (E2) varying the flow rate of the inner phase and/or of the outer phase to modify the flow profile, namely:

in the case where the flow rates D1 and D2 in said step (E1) lead to drops of the inner phase in the outer phase: modifying the flow rate of the inner phase and/or of the outer phase until the formation of a continuous jet of the inner phase in the outer phase is obtained; and         in the case where the flow rates D1 and D2 in said step (E1) lead to a jet of the inner phase in the outer phase: modifying the flow rate of the inner phase and/or of the outer phase until the formation of drops of the inner phase in the outer phase is obtained;

and identifying a transition pair of values of the flow rate of the inner and outer phases, on the basis of which the modification of the flow profile takes place from drops to jet or from jet to drops, and     in said step (E3), on the basis of the transition pair identified in said step (E2),         calculating the value of interfacial tension between the two fluid phases, inner and outer; or         comparing the transition pair obtained in said step (E2) with the transition pair for another system of fluid phases in the critical phase determined under the same conditions, to obtain a relative indication between the values of interfacial tension of the two systems.

18. The method as claimed in claim 17, where said steps (E1) and (E2) are conducted in succession, under the same conditions, firstly with a first pair of fluid phases, and then for a second pair of fluid phases, and then the results obtained in the two cases are compared in said step (E3), whereby the first pair is compared with the second pair.

19. The method as claimed in claim 17, wherein the inner flow member (2) and the outer flow member (4) are two coaxial capillary tubes, wherein an outer diameter of the inner capillary tube is between 10 micrometers and 2 millimeters and the inner diameter of the outer flow member is between 50 micrometers and 4 millimeters, and a ratio of the inner diameter of the outer flow member to the outer diameter of the inner flow member is between 1.1 and 10.

20. The method according to claim 17, wherein at least one of the pairs employed comprises crude petroleum, within supercritical $CO_2$.

\* \* \* \* \*